ize et al.

United States Patent [19]

Lesher et al.

[11] 4,304,776
[45] Dec. 8, 1981

[54] 4-SUBSTITUTED-6-(PYRIDINYL)-3(2H)-PYRIDAZINONES AND THEIR USE AS INTERMEDIATES AND CARDIOTONICS

[75] Inventors: George Y. Lesher, Schodack; William B. Dickinson, Albany, both of N.Y.

[73] Assignee: Sterling Drug Inc., New York, N.Y.

[21] Appl. No.: 144,697

[22] Filed: Apr. 28, 1980

[51] Int. Cl.³ .................. C07D 401/04; A61K 31/50
[52] U.S. Cl. .................................. 424/250; 544/238; 546/315; 546/314
[58] Field of Search .................. 544/238; 424/250

[56] References Cited

PUBLICATIONS

Kogimin et al., Chem. Abs. 76, 24731; (1971).

Primary Examiner—Mark L. Berch
Attorney, Agent, or Firm—Robert K. Bair; B. Woodrow Wyatt

[57] ABSTRACT

2-R-4-R'-6-PY-3(2H)-pyridazinones (I) or salts thereof, which are useful as intermediates and some as cardiotonics, are prepared by reacting di-(lower-alkyl) hydroxy[2-oxo-2-PY-ethyl]propanedioate (II) with a hydrazine salt of the formula $RNHNH_2.nH_xAn$ (III) to produce lower-alkyl 2,3-dihydro-2-R-3-oxo-6-PY-4-pyridazinecarboxylate (Ia where R' is lower-carbalkoxy) and reacting Ia with hydrazine hydrate or anhydrous hydrazine to produce 2,3-dihydro-2-R-3-oxo-6-PY-4-pyridazinecarboxylic acid hydrazide (Ib where R' is aminocarbamyl), where PY is 4- or 3-pyridinyl or 4- or 3-pyridinyl having one or two lower-alkyl substituents, R is hydrogen, lower-alkyl or lower-hydroxyalkyl, R' is carbamyl, carboxy, aminocarbamyl or lower-carbalkoxy, n is 1 or 2, x is 1, 2 or 3, and An is an anion of a strong inorganic acid or an organic sulfonic acid. Also shown are: the preparation of II from PY—COCH₃ (IV), the conversion of Ia to Ib (Id where R' is carboxy), and the use of 2-R-4-R"-6-PY-3(2H)-pyridazinones (I where R is lower-alkyl or lower-hydroxyalkyl and R" is carbamyl, aminocarbamyl or lower-carbalkoxy) as cardiotonic agents. Other intermediates are shown.

8 Claims, No Drawings

4-SUBSTITUTED-6-(PYRIDINYL)-3(2H)-PYRIDAZINONES AND THEIR USE AS INTERMEDIATES AND CARDIOTONICS

CROSS-REFERENCE TO RELATED APPLICATION 4,5-Dihydro-6-(4-pyridinyl)-3-pyridazinol, tautomeric with 4,5-dihydro-6-(4-pyridinyl)-3(2H)-pyridazinone, is disclosed and claimed in copending Application Ser. No. 71,064, filed Aug. 30, 1979. Also disclosed and claimed is the process which comprises reacting γ-oxo-γ-(4-pyridinyl)butyronitrile with a hydrazine salt of a strong inorganic or organic sulfonic acid to produce 4,5-dihydro-6-(4-pyridinyl)-3-pyridazinol. Also shown and claimed is the use of 4,5-dihydro-6-(4-pyridinyl)-3-pyridazinol in lowering blood pressure. 4,5-Dihydro-6-(4-pyridinyl)-3-pyridazinol or tautomeric 4,5-dihydro-6-(4-pyridinyl)-3(2H)-pyridazinone also is disclosed as an intermediate in copending U.S. patent application Ser. No. 144,563, Apr. 28, 1980.

Copending U.S. patent application Ser. No. 144,564, filed Apr. 28, 1980 and now abandoned in favor of its copending continuation-in-part Application Ser. No. 243,472, filed Mar. 13, 1981, discloses and claims 2-R-4,5-dihydro-6-PY-3(2H)-pyridazinones and their use as cardiotonics, where R is lower-alkyl or lower-hydroxyalkyl and PY is 4- or 3-pyridinyl or 4- or 3-pyridinyl having one or two lower-alkyl substituents. Said 2-R-4,5-dihydro-6-PY-3(2H)-pyridazinones also are disclosed as intermediates in copending U.S. patent application Ser. No. 144,563, Apr. 28, 1980.

6-(4-Pyridinyl)-3-pyridazinol, tautomeric with 6-(4-pyridinyl)-3(2H)-pyridazinone and its preparation from 4,5-dihydro-6-(4-pyridinyl)-3-pyridazinol are disclosed and claimed in copending application Ser. No. 71,065, filed Aug. 30, 1979 and now abandoned and its copending continuation-in-part application Ser. No. 144,576, filed Apr. 28, 1980. Also shown and claimed is the use of 6-(4-pyridinyl)-3-pyridazinol as a cardiotonic. 6-(4-Pyridinyl-3-pyridazinol or tautomeric 6-(4-pyridinyl)-3(2H)-pyridazinone also is disclosed as an intermediate in copending U.S. patent application Ser. No. 144,563, Apr. 28, 1980.

Copending U.S. patent application Ser. No. 144,576, filed Apr. 28, 1980, a continuation-in-part-of said copending application Ser. No. 71,065, discloses and claims 2-R-6-PY-3(2H)-pyridazinones and their use as cardiotonics, where R is hydrogen, lower-alkyl or lower-hydroxyalkyl, and PY is 4- or 3-pyridinyl or 4- or 3-pyridinyl having one or two lower-alkyl substituents. Said 2-R-6-PY-3(2H)-pyridazinones also are disclosed as intermediates in copending application Ser. No. 144,563, filed even date herewith.

Copending Application Ser. No. 238,483, filed Feb. 26, 1981, a division of instant application Ser. No. 144,697, claims the hereinbelow-disclosed process aspects of the invention originally disclosed and claimed herein.

BACKGROUND OF THE INVENTION (a) Field of the invention

This invention relates to 6-(pyridinyl)-4-substituted-3(2H)-pyridazinones, useful as cardiotonic agents, to their preparation, and to their use as cardiotonic agents.

(b) Description of the Prior Art

Haginiwa et al. [Yakugaku Zasshi 98 (1), 67–71 (1978); Chem. Abstrs. 88, 170,996v (1978)] reacted 3(2H)-pyridazinone with pyridine 1-oxide and platinized Pd-C catalyst to produce 6-(2-pyridinyl)-3(2H)-pyridazinone.

Yoshitomi Pharmaceutical Ind., Ltd. Japanese patent application Disclosure No. 19,987/79, published Feb. 15, 1979 and based on application No. 85,192/77, filed July 15, 1977, discloses, inter alia, the preparation of 4,5-dihydro-6-(4-pyridinyl)-3(2H)-pyridazinone by refluxing for two hours an ethanolic solution of 3-(isonicotinoyl)propanoic acid [same as γ-oxo-γ-(4-pyridinyl)butyric acid] and hydrazine hydrate. 4,5-Dihydro-6-(4-pyridinyl)-3(2H)-pyridazinone and closely related 4,5-dihydro-6-(4- or 3- or 2-pyridinyl)-5-R-3(2H)-pyridazinones, where R is H or lower alkyl, are said (page 2 of English translation) to be "useful not only as medicines such as hypotensive and antithrombus agents because they have pharmacological actions such as hypotensive, blood platelet coagulation-inhibitory and membrane-stabilizing actions, but also as intermediates for the synthesis of such medicines".

SUMMARY OF THE INVENTION

In a composition of matter aspect, the invention relates to 2-R-4-R'-6-PY-3(2H)-pyridazinones (I) or pharmaceutically-acceptable acid-addition salts thereof, useful as cardiotonic agents, to their preparation and to their use as intermediates and/or as cardiotonics, where R, R' and PY are defined hereinbelow.

In a process aspect the invention comprises reacting di-(lower-alkyl)hydroxy[2-oxo-2-PY-ethyl]propanedioate (II) with a hydrazine or substituted-hydrazine salt RNHNH$_2$·nH$_x$An (III), to produce lower-alkyl 2,3-dihydro-2-R-3-oxo-6-PY-4-pyridazinecarboxylate (Ia where R' is lower-carbalkoxy) and reacting Ia with hydrazine hydrate or anhydrous hydrazine to produce 2,3-dihydro-2-R-3-oxo-6-PY-4-pyridazinecarboxylic acid hydrazide (Ib where R' is aminocarbamyl), where R, PY, n and x are defined below. Other process aspects of the invention comprises each of the above steps, i.e., II to Ia and Ia to Ib.

Other process aspects of the invention comprise converting Ia to 2,3-dihydro-2-R-3-oxo-6-PY-4-pyridazinecarboxamide (Ic where R' is carbamyl) either directly or via the corresponding 2,3-dihydro-2-R-3-oxo-6-PY-4-pyridazinecarboxylic acid (Id where R' is carboxy).

Another composition of matter aspect of the invention are the di-(lower-alkyl)hydroxy[2-oxo-2-PY-ethyl]-propanedioates (II), which as shown above are useful as intermediates for preparing Ia.

Another process aspect of the invention comprises reacting acetylpyridine, PY—COCH$_3$ (IV), with di-(lower-alkyl)oxomalonate to produce said intermediate di-(lower-alkyl)hydroxy[2-oxo-2-PY-ethyl]propanedioate (II).

A composition aspect of the invention relates to a cardiotonic composition for increasing cardiac contractility, said composition comprising a pharmaceutically-acceptable inert carrier and, as the active component thereof, an effective amount of the cardiotonic 2-R-4-R"-6-PY-3-(2H)-pyridazinone or pharmaceutically-acceptable acid-addition salt thereof, where R" is defined hereinbelow.

In a method aspect, the invention relates to a method for increasing cardiac contractility in a patient requiring such treatment which comprises administering orally or parenterally in a solid or liquid dosage form to such patient an effective amount of the cardiotonic 2-R-4-R''-6-PY-3(2H)-pyridazinone or pharmaceutically-acceptable acid-addition salt thereof.

DETAILED DESCRIPTION INCLUSIVE OF PREFERRED EMBODIMENTS

In a composition of matter aspect the invention resides in the 2-R-4-R'-6-PY-3(2H)-pyridazinones having formula I

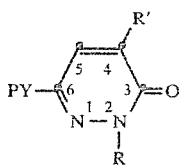

or pharmaceutically-acceptable acid-addition salts thereof, where PY is 4- or 3-pyridinyl or 4- or 3-pyridinyl having one or two lower-alkyl substituents, R is hydrogen, lower-alkyl or lower-hydroxyalkyl, and R' is carbamyl, carboxy, aminocarbamyl or lower-carbalkoxy. The compounds of formula I except those where R' is carboxy or those where R' is lower-carbalkoxy when R is hydrogen are useful as cardiotonic agents, as determined by standard cardiotonic evaluation procedures; the compounds of formula I where R' is carboxy or where R' is lower-carbalkoxy when R is hydrogen are useful as intermediates, e.g., in preparing the corresponding compounds where R' is carbamyl. Also, the compounds where R' are carbamyl or aminocarbamyl are useful as intermediates in preparing the compounds of formula I where R' is amino, said process and compounds being disclosed herein, and disclosed and claimed in copending application Ser. No. 144,563, filed Apr. 28, 1980. Preferred embodiments are those of formula I where R is hydrogen, methyl or ethyl, R' is carbamyl or aminocarbamyl and PY is 4-pyridinyl or 3-pyridinyl.

The compounds of formula I where R is hydrogen may exist in tautomeric forms, that is, as 4-R'-6-PY-3(2H)-pyridazinones of formula I and/or as 4-R'-6-PY-3-pyridazinols of formula IA, illustrated as follows

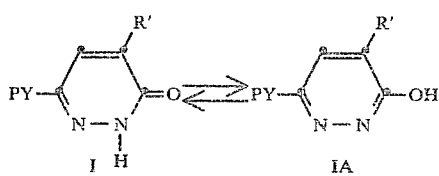

Structural preferences for known 3(2H)-pyridazinones or 3-pyridazinols would indicate the above formula I to be the preferred tautomeric structure; thus, we have preferred to use the names based on structure I, although it is understood that either or both structures are comprehended herein.

In a process aspect the invention resides in the process which comprises reacting di-(lower-alkyl)hydroxy[2-oxo-2-PY-ethyl]propanedioate (II) with a hydrazine salt of the formula RNHNH$_2$.nH$_x$An (III) to produce lower-alkyl 2,3-dihydro-2-R-3-oxo-6-PY-4-pyridazinecarboxylate (Ia where R' is lower-carbalkoxy), and reacting Ia with hydrazine hydrate or anhydrous hydrazine to produce 2,3-dihydro-2-R-3-oxo-6-PY-4-pyridazinecarboxylic acid hydrazide (Ib where R' is aminocarbamyl), where PY and R are defined as above for formula I, preferably 4-pyridinyl and hydrogen or methyl, respectively, n is 1 or 2, x is 1, 2 or 3, and An is an anion of a strong inorganic acid or an organic sulfonic acid. Other process aspects of the invention resides in each of the above steps, i.e., II to Ia and Ia to Ib.

Other process aspects of the invention reside in the process of converting lower-alkyl 2,3-dihydro-2-R-3-oxo-6-PY-4-pyridazinecarboxylate (Ia where R' is lower-carbalkoxy) to 2,3-dihydro-2-R-3-oxo-6-PY-4-pyridazinecarboxamide (Ic where R' is carbamyl) either directly by reaction with ammonia or via the corresponding 2,3-dihydro-2-R-3-oxo-6-PY-4-pyridazinecarboxylic acid (Id where R' is carboxy) by hydrolyzing the ester to acid, reacting the acid with a chlorinating agent to form the acid chloride and reacting the latter with ammonia to form said carboxamide (Ic where R' is carbamyl), where R and PY have the meanings given above for formula I, preferably hydrogen or methyl and 4-pyridinyl, respectively.

Another composition of matter aspect of the invention resides in the di-(lower-alkyl)hydroxy[2-oxo-2-PY-ethyl]propanedioates of formula II

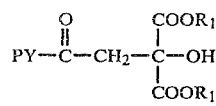

or pharmaceutically-acceptable acid-addition salt thereof where PY is defined as above for formula I, preferably 4-pyridinyl, or 3-pyridinyl and R$_1$ is lower-alkyl, preferably ethyl or methyl.

Another aspect of the invention resides in the process which comprises reacting acetylpyridine of the formula PY—COCH$_3$ (IV) with di-(lower-alkyl)oxomalonate to produce di-(lower-alkyl)hydroxy[2-oxo-2-PY-ethyl]propanedioate (II) where PY is defined as in formula I above, preferably 4-pyridinyl.

A composition aspect of the invention resides in the cardiotonic composition for increasing cardiac contractility, said composition comprising a pharmaceutically-acceptable inert carrier and, as the active component thereof, an effective amount of a cardiotonic 2-R-4-R''-6-PY-3(2H)-pyridazinone of formula I where R is lower-alkyl or lower-hydroxyalkyl, PY is defined as in formula I and R'' is carbamyl, aminocarbamyl or lower-carbalkoxy, or pharmaceutically-acceptable acid-addition salt thereof. Preferred embodiments are those where PY is 4-pyridinyl or 3-pyridinyl.

In a method aspect, the invention resides in the method for increasing cardiac contractility in a patient requiring such treatment which comprises administering orally or parenterally in a solid or liquid dosage form to such patient an effective amount of a cardiotonic 2-R-4-R''-6-PY-3(2H)-pyridazinone or pharmaceutically-acceptable acid-addition salt thereof, where R is lower-alkyl or lower-hydroxyalkyl, PY is defined as in formula I and R'' is carbamyl, aminocarbamyl or lower-carbalkoxy. Preferred embodiments are those where PY is 4-pyridinyl or 3-pyridinyl.

The term "lower-alkyl" as used herein, e.g., as one of the meanings for R (formulas I, Ia, Ib, Ic, III), the meaning for R$_1$ (formula II) or as a substituent for PY (formula I, Ia, Ib, Ic, Id or II) means alkyl radicals having from one to six carbon atoms which can be arranged as straight or branched claims, illustrated by methyl, ethyl, n-propyl, isopropyl, n-butyl, 2-butyl, isobutyl.

The symbol PY as used here, e.g., as the 6-substituent in the compounds having formulas I, Ia, Ib, Ic, Id or II, means 4- or 3-pyridinyl or 4- or 3-pyridinyl having one or two "lower-alkyl" substituents, illustrated by 2-methyl-4-pyridinyl, 2,6-dimethyl-4-pyridinyl, 3-methyl-4-pyridinyl, 2-methyl-3-pyridinyl, 6-methyl-3-pyridinyl (alternatively named 2-methyl-5-pyridinyl, 2,3-dimethyl-4-pyridinyl, 2,6-dimethyl-4-pyridinyl, 2-ethyl-4-pyridinyl, 2-isopropyl-4-pyridinyl, 2-n-butyl-4-pyridinyl, 2-n-hexyl-4-pyridinyl, 2,6-diethyl-4-pyridinyl, 2,6-diethyl-3-pyridinyl, 2,6-diisopropyl-4-pyridinyl, 2,6,di-n-hexyl-4-pyridinyl, and the like.

The term "lower-hydroxyalkyl", as used herein, e.g., as one of the meanings for R in formulas I, Ia, Ib, Ic, Id or III, means hydroxyalkyl radicals having form two to six carbon atoms and having its hydroxy group and its free valence bond (or connecting linkage) on different carbon atoms which can be arranged as straight or branched chains, illustrated by 2-hydroxyethyl, 2-hydroxypropyl, 3-hydroxypropyl, 2-hydroxy-2-methylpropyl, 2-hydroxy-1,1-dimethylethyl, 4-hydroxybutyl, 5-hydroxyamyl, 6-hydroxyhexyl, and the like.

The term "lower-carbalkoxy", as used herein, as one of the meanings for R' in formulas I and Ia, means carbalkoxy radicals where the alkoxy portion can be straight or branch-chained and has from one to six carbon atoms, as illustrated by carbomethoxy, carbethoxy, carbo-n-propoxy, carbisopropoxy, carbo-n-butoxy, carbo-tert.-butoxy and carbo-n-hexoxy.

The compounds of the invention having formulas I, Ia, Ib, Ic, and II are useful both in the free base form and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial cardiotonic properties inherent in the free base of the cardiotonically-active compounds of the invention are not vitiated by side effects ascribable to the anions. In practicing the invention, it is convenient to use the free base form; however, appropriate pharmaceutically-acceptable salts within the scope of the invention are those derived from mineral acids such as hydrochloric acid, sulfuric acid, phosphoric acid and sulfamic acid; and organic acid such as acetic acid, citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate, respectively.

The acid-addition salts of said basic compound are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically-acceptable salts of said basic compound are preferred, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a pharmaceutically-acceptable salt by ion exchange procedures.

The molecular structures of the compounds of the invention were assigned on the basis of evidence provided by infrared, nuclear magnetic resonance and mass spectra, and by the correspondence of calculated and found values for the elemental analyses.

The manner of making and using the instant invention will now be generally described so as to enable a person skilled in the art of pharmaceutical chemistry to make and use the same, as follows.

The reaction of acetylpyridine of the formula PY—COCH$_3$ (IV) with di-(lower-alkyl)oxomalonate to produce di-(lower-alkyl)hydroxy[2-oxo-2-PY-ethyl]propanedioate (II), where PY is defined as in formula I above, is carried out by heating the reactants at about 80° C. to 120° C., preferably about 90° C. to 110° C. The reaction is conveniently run on a steam bath. The reaction is preferably run using diethyl or dimethyl oxomalonate. This preparation is illustrated hereinbelow in Examples A-1 through A-9.

The preparation of lower-alkyy 2,3-dihydro-2-R-3-oxo-6-PY-4-pyridazinecarboxylates by reacting di-(lower-alkyl)hydroxy[2-oxo-2-PY-ethyl]propanedioate (II) with a hydrazine salt of the formula RNHNH$_2$.nH$_x$An (III), where PY and R are defined as in formula I above and n, x and An are defined as in formula III above, is carried out by heating the reactants at about 60° C. to 100° C., preferably about 75° C. to 85° C., and preferably in the presence of a suitable solvent, e.g., a lower-alkanol such as methanol, ethanol or isopropyl alcohol. Other suitable solvents would be dioxane, tetrahydrofuran, pyridine, ethylene glycol, and the like. Preferred R-hydrazine salts are the dihydrochlorides or sulfates. This preparation is illustrated below in Examples C-2 through C-17. Also note Example B-1 where diethyl hydroxy[2-oxo-2-(4-pyridinyl)ethyl]propanedioate was refluxed with hydrazine monohydrochloride in methanol for a relatively short period (less than 2 hours) to produce ethyl 2,3,4,5-tetrahydro-4-hydroxy-3-oxo-6-(4-pyridinyl)-4-pyridazinecarboxylate which, as shown in Example C-1, was readily dehydrated by treating a solution of it in a suitable solvent, e.g., acetonitrile, ethanol, tetrahydrofuran or dioxane with hydrogen chloride to produce ethyl 2,3-dihydro-3-oxo-6-(4-pyridinyl)-4-pyridazinecarboxylate.

The conversion of the lower-alkyl 2,3-dihydro-2-R-3-oxo-6-PY-4-pyridazinecarboxylate (Ia) to the corresponding 4-pyridazinecarboxamide (Ic) was conveniently carried out by bubbling ammonia into a solution of Ia in an inert appropriate solvent, e.g., a lower-alkanol, preferably ethanol or methanol. Other solvents include isopropyl alcohol, acetonitrile, tetrahydrofuran, dioxane and the like. The reaction is readily run at room temperature. This preparation is illustrated below in Examples D-1 through D-16.

The conversion of lower-alkyl 2,3-dihydro-2-R-3-oxo-6-PY-pyridazinecarboxylate (Ia) to the corresponding 2,3-dihydro-2-R-3-oxo-6-PY-pyridazinecarboxylic acid hydrazine (Ib) by reaction with hydrazine hydrate or anhydrous hydrazine is carried out by heating the reactants at about 60° C. to about 100° C., preferably about 75° C. to 85° C. in a suitable solvent, e.g., a lower-alkanol, preferably methanol, ethanol or isopropyl alcohol. Other suitable solvents include pyridine, tetrahydrofuran, dioxane and the like. This preparation is illustrated below in Examples E-1 through E-16.

The hydrolysis of lower-alkyl 2,3-dihydro-2-R-3-oxo-6-PY-pyridazinecarboxylate (Ia) to the corresponding carboxylic acid (Id) is carried out by heating the ester (Ia) with aqueous alkali metal hydroxide solution, e.g., preferably aqueous sodium hydroxide solution, conveniently done by heating the reactants on a steam bath. Alternatively, the hydrolysis of said 4-pyridazinecarboxylate (Ia) to 4-pyridazinecarboxylic acid (Id) can be carried out by heating the ester (Ia) with an aqueous solution of a strong inorganic acid, e.g., hydrochloric acid, sulfuric acid, and the like. This hydrolysis is illustrated below in Examples F-1 through F-16.

The conversions of 2,3-dihydro-3-oxo-6-PY-4-pyridazinecarboxylic acid hydrazide (Ib) or corresponding 2,3-dihydro-2-R-3-oxo-6-PY-4-pyridazinecarboxamide to 4-amino-2-R-6-PY-3(2H)-pyridazinone by reaction, respectively, with nitrous acid or alkali hypohalite and the conversion of 2-R-6-PY-3(2H)-pyridazinone to 4-amino-2-R-6-PY-3(2H)-pyridazinone by reaction with hydrazine, as well as said 4-amino-2-R-6-PY-3(2H)-pyridazinones and their use as cardiotonic agents, are disclosed and claimed in copending U.S. patent application Ser. No. 144563 filed on even date herewith. These conversions and resulting compounds are illustrated below in Examples G-1 through G-61.

The preparation of the intermediate 4,5-dihydro-2-(lower-alkyl)-6-PY-3(2H)-pyridazinones by reacting a 4-oxo-4-PY-butanenitrile with N-R-hydrazine salt of a strong inorganic acid or organic sulfonic acid, the resulting 4,5-dihydro-2-(lower-alkyl or lower-hydroxyalkyl)-6-PY-3(2H)-pyridazinones and their use as cardiotonic agents are disclosed and claimed in copending U.S. patent application Ser. No. 144,564, filed Apr. 28, 1970 and now abandoned in favor of copending Application Ser. No. 243,472, filed Mar. 13, 1981, and, are illustrated below in Examples H-1 through H-10 and H-17 through H-21.

The preparation of the intermediate 4,5-dihydro-6-PY-3(2H)-pyridazinones or tautomeric 4,5-dihydro-6-PY-3-pyridazinols by reacting 4-oxo-4-PY-butanenitrile is illustrated below in Examples H-11 through H-16. Example H-11 is disclosed as Example 1 in each of copending applications Ser. Nos. 71,064 and 71,065 abn, each filed Aug. 30, 1979; and, compound and salts of Example H-11 are claimed in application Ser. No. 71,064.

The intermediate 4-oxo-4-PY-butanenitriles are generally known compounds, e.g., Stetter et al., Chem. Ber. 107, 210 (1974), and are prepared by generally known methods. Preparation of these compounds is illustrated below in Examples J-1 thru J-6.

The conversion of the intermediate 4,5-dihydro-2-R-6-PY-3(2H)-pyridazinones or where R is H the tautomeric 4,5-dihydro-6-PY-3-pyridazinols by reaction with bromine to the corresponding intermediate 2-R-6-PY-3(2H)-pyridazinones, the latter 2-R-6-PY-3(2H)-pyridazinones and their use as cardiotonics are disclosed and claimed in copending application Ser. No. 144,576, a continuation-in-part of said application Ser. No. 71,065, filed Apr. 28, 1980, and, are illustrated below in Examples I-1 through I-16. Example I-11 is disclosed as Example 2 in each of copending U.S. Patent applications Ser. Nos. 71,064 and 71,065 abn each filed Aug. 30, 1979; and the compound and salts of Example I-11 are presently claimed in application Ser. No. 144,576.

The following examples will further illustrate the invention without, however, limiting it thereto.

A. Di-(lower-alkyl) Hydroxy[2-oxo-2-(pyridinyl)ethyl]propanedioates

A-1. Diethyl hydroxy[2-oxo-2-(4-pyridinyl)ethyl]propanedioate—A mixture containing 8.71 g. of diethyl oxomalonate and 6.06 g. of 4-acetylpyridine was heated on a steam bath for 3 hours and then cooled. A small sample of the reaction mixture in a small test tube was partially solidified by rubbing the sample with a glass rod against the inside of the test tube. The remainder of the cooled reaction mixture was dissolved in 13 ml. of methanol, the solution chilled and seeded with crystals formed in the small test tube and the resulting mixture was allowed to solidify. The solid was collected and washed with small quantity of methanol and air dried to yield 4.7 g. of diethyl hydroxy[2-oxo-2-(4-pyridinyl)ethyl]propanedioate, m.p. 130°–131.5° C. More product was obtained from the mother liquor as follows: the above filtrate was evaporated to dryness on a rotary evaporator while heating on a steam bath and the residue was heated for an additional hour on said bath. Since the residue had not solidified, a small sample in a test tube when covered with ethanol and seeded with the above product gave a solid. The solid was dissolved in a minimum amount warm ethanol, the resulting solution concentrated briefly on a steam bath and then chilled. The resulting solid was collected, washed with a small quantity of ethanol and air-dried to yield another 4.4 g. of diethyl hydroxy[2-oxo-2-(4-pyridinyl)ethyl]propanedioate, m.p. 127°–130° C. The combined two crops (4.7+4.4=9.1 g. or 61.7% yield) was dissolved in about 23 ml. of hot methanol and the solution then chilled thoroughly. The separated white solid was rinsed with a little methanol, air-dried briefly and then dried at 25° C. over $P_2O_5$ at 10 mm. over the weekend, thereby yielding 7.4 g. of diethyl hydroxy[2-oxo-2-(4-pyridinyl)ethyl]propanedioate, m.p. 131°–132° C.

Following the procedure described in Example A-1 but using in place of 4-acetylpyridine a corresponding molar equivalent quantity of the appropriate 3- or 4-acetylpyridine, it is contemplated that there can be obtained the corresponding diethyl hydroxy[2-oxo-2-(pyridinyl)ethyl]propanedioates of Examples A-2 thru A-6.

A-2. Diethyl hydroxy[2-oxo-2-(3-pyridinyl)ethyl]propanedioate using 3-acetylpyridine.

A-3. Diethyl hydroxy[2-oxo-2-(2-methyl-3-pyridinyl)ethyl]propanedioate using 3-acetyl-2-methylpyridine.

A-4. Diethyl hydroxy[2-oxo-2-(5-methyl-3-pyridinyl)ethyl]propanedioate using 3-acetyl-5-methylpyridine.

A-5. Diethyl hydroxy[2-oxo-2-(3-ethyl-4-pyridinyl)ethyl]propanedioate using 4-acetyl-3-ethylpyridine.

A-6. Diethyl hydroxy[2-oxo-2-(2,6-dimethyl-4-pyridinyl)ethyl]propanedioate using 4-acetyl-2,6-dimethyl-pyridine.

Following the procedure described in Example A-1 but using in place of diethyl oxomalonate a molar equivalent quantity of the appropriate di-(lower-alkyl) oxomalonate, it is contemplated that there can be obtained the corresponding di-(lower-alkyl) esters of Examples A-7 through A-9.

A-7. Dimethyl hydroxy[2-oxo-2-(4-pyridinyl)ethyl]propanedioate.

A-8. Di-n-propyl hydroxy[2-oxo-2-(4-pyridinyl)-ethyl]propanedioate.

A-9. Diisobutyl hydroxy[2-oxo-2-(4-pyridinyl)-ethyl]propanedioate.

B. Lower-alkyl 2,3,4,5-Tetrahydro-2-R-4-hydroxy-3-oxo-6-PY-4-pyridazinecarboxylates B-1. Ethyl 2,3,4,5-Tetrahydro-4-hydroxy-3-oxo-6-(4-pyridinyl)-4-pyridazinecarboxylate—A 5.9 g. portion of diethyl hydroxy[2-oxo-2-(4-pyridinyl)ethyl]propanedioate was added to a warm solution containing 1.4 g. of hydrazine monohydrochloride in 150 ml. of methanol, the resulting reaction mixture was refluxed gently for 1 hour and 45 minutes, cooled briefly and then stripped to dryness on a roto vaporizer. The resulting gummy residue was warmed with a small quantity of acetonitrile to produce a crystalline material; the mixture was then chilled. The crystals were collected, washed with a small quantity of acetonitrile and air-dried to yield 2.25 g. ethyl 2,3,4,5-tetrahydro-4-hydroxy-3-oxo-6-(4-pyridinyl)-4-pyridazinecarboxylate hydrochloride, m.p. 160°-163° C. with decomposition. A 1.65 g. portion of this monohydrochloride was dissolved in about 10 ml. of water, the solution filtered and solid sodium bicarbonate was added in small portions until the evolution of carbon dioxide ceased. The precipitated white solid was collected, rinsed with water and dried over $P_2O_5$ at 10 mm. and 25° C. for six hours to yield 1.2 g. of ethyl 2,3,4,5-tetrahydro-4-hydroxy-3-oxo-6-(4-pyridinyl)-4-pyridazine-carboxylate, m.p. 193°-195° C. with decomposition.

As shown in Example C-1, the 4-hydroxy-tetrahydro product of the immediately preceding paragraph is readily dehydrated by treating it with a strong inorganic acid or an organic sulfonic acid, preferably hydrogen chloride, to produce ethyl 2,3-dihydro-3-oxo-6-(4-pyridinyl)-4-pyridazinecarboxylate. Thus, it appears that the conversions shown in Examples C-2 through C-17 go through the corresponding lower-alkyl 2,3,4,5-tetrahydro-4-hydroxy-3-oxo-6-PY-4-pyridazinecarboxylates, none of which was actually isolated other than the product of Example B-1.

C. Lower-alkyl 2,3-Dihydro-2-R-3-oxo-6-PY-4-pyridazinecarboxylates

C-1. Ethyl 2,3-Dihydro-3-oxo-6-(4-pyridinyl)-4-pyridazinecarboxylates—This preparation shows the conversion of Example B-1 to the entitled compound. Into a one liter portion of acetonitrile was bubbled gaseous hydrogen chloride with stirring for about 5 minutes. To this mixture was added 9.5 g. of ethyl 2,3,4,5-tetrahydro-4-hydroxy-3-oxo-6-(4-pyridinyl)-4-pyridazinecarboxylate and hydrogen chloride was bubbled into the mixture for an additional 15 minutes. The reaction mixture was stirred for 1 hour whereupon the solid separated. The reaction mixture was stirred for an additional 2 hours and then allowed to stand at room temperature overnight (about 15 hours). The white solid was collected, dried in a vacuum oven for 2 hours at 40° C. over $P_2O_5$ to yield 8.0 g. of ethyl 2,3-dihydro-3-oxo-6-(4-pyridinyl)-4-pyridazinecarboxylate dihydrochloride, m.p. 212°-220° C. with decomposition. The hydrochloride salt was dissolved in a minimum quantity of water and solution basified with solid sodium bicarbonate. The resulting precipitate was collected, washed with water and dried in a vacuum oven over $P_2O_5$ at 25° C. overnight to yield 5.5 g. of ethyl, 2,3-dihydro-3-oxo-6-(4-pyridinyl)-4-pyridazinecarboxylate, m.p. 196°-197° C.

C-2. Ethyl 2,3-Dihydro-3-oxo-6-(4-pyridinyl)-4-pyridazinecarboxylate—The following synthesis of the entitled compound was carried out directly using Example A-1. To a warm solution containing 16.0 g. of hydrazine dihydrochloride in 1 l. of absolute ethanol was added with stirring 44.25 g. of diethyl hydroxy[2-oxo-2-(4-pyridinyl)-ethyl]propanedioate rinsed in with 250 ml. of absolute ethanol and the resulting reaction mixture was refluxed for 19 hours. About 300 ml. of the ethanol was distilled off under reduced pressure and the remaining reaction mixture was evaporated on a roto vaporizer to obtain a tan solid. The solid was slurried with 100 ml. of water and the mixture transferred to a 500 ml. flask, rinsing the material with an additional 25 ml. of water. To the aqueous mixture was cautiously added solid sodium bicarbonate until evolution of carbon dioxide ceased. The solid was collected, rinsed with water, air-dried and then dried in a vacuum oven over $P_2O_5$ at 10 mm. in 25° C. to yield ethyl 2,3-dihydro-3-oxo-6-(4-pyridinyl)-4-pyridazinecarboxylate.

C-3. Ethyl 2,3-Dihydro-2-methyl-3-oxo-6-(4-pyridinyl)-4-pyridazinecarboxylate—A mixture containing 26 g. of 1-methylhydrazine dihydrochloride, 148 g. of diethyl hydroxy[2-oxo-2-(4-pyridinyl)ethyl]propanedioate in 1500 ml. of absolute ethanol was refluxed with stirring overnight (about 15 hours), the reaction mixture was heated in vacuo to remove the solvent and the residual gummy material was taken up in about 600 ml. of water and the aqueous solution basified with solid potassium carbonate until basic to litmus. The precipitated solid was collected and later combined with additional product obtained from the filtrate which had been found to still be acidic. The filtrate was basified with 10% aqueous potassium carbonate and the alkaline mixture was extracted with chloroform and the chloroform extract heated in vacuo to remove the solvent. The resulting solid product was combined with the above-said product and the combined material was recrystallized from ethyl acetate and n-hexane and dried first at 40° C. for 17 hours and then at 60° C. for 17 hours to produce 34 g. of ethyl 2,3-dihydro-2-methyl-3-oxo-6-(4-pyridinyl)-4-pyridazinecarboxylate, m.p. 128°-129° C.

Acid-addition salts of ethyl 2,3-dihydro-2-methyl-3-oxo-6-(4-pyridinyl)-4-pyridazinecarboxylate are conveniently prepared by adding to a mixture of 1 g. of ethyl 2,3-dihydro-2-methyl-3-oxo-6-(4-pyridinyl)-4-pyridazinecarboxylate in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Alternatively, the lactate or hydrochloride acid-addition salt of ethyl 2,3-dihydro-2-methyl-3-oxo-6-(4-pyridinyl)-4-pyridazinecarboxylate is conveniently prepared in aqueous solution by adding to water with stirring molar equivalent quantities each of ethyl 2,3-dihydro-2-methyl-3-oxo-6-(4-pyridinyl)-4-pyridazinecarboxylate and lactic acid or hydrochloric acid, respectively.

Following the procedure described above in Example C-2 but using in place of diethyl hydroxy[2-oxo-2-(4-pyridinyl)ethyl]propanedioate a molar equivalent quantity of the appropriate diethyl hydroxy[2-oxo-2-(pyridinyl)ethyl]propanedioate, it is contemplated that there can be obtained the corresponding ethyl 2,3-dihydro-3-oxo-6-(pyridinyl)-4-pyridazinecarboxylates of Examples C-4 thru C-8.

C-4. Ethyl 2,3-dihydro-3-oxo-6-(3-pyridinyl)-4-pyridazinecarboxylate.

C-5. Ethyl 2,3-dihydro-6-(2-methyl-3-pyridinyl)-3-oxo-4-pyridazinecarboxylate.

C-6. Ethyl 2,3-dihydro-6-(5-methyl-3-pyridinyl)-3-oxo-4-pyridazinecarboxylate.

C-7. Ethyl 6-(3-ethyl-4-pyridinyl)-2,3-dihydro-3-oxo-4-pyridazinecarboxylate.

C-8. Ethyl 2,3-dihydro-6-(2,6-dimethyl-4-pyridinyl)-3-oxo-4-pyridazinecarboxylate.

Following the procedure described in Example C-3 but using in place of 1-methylhydrazine dihydrochloride a molar equivalent quantity of the corresponding 1-R-hydrazine dihydrochloride or other salt of a strong inorganic acid or an organic sulfonic acid, it is contemplated that there can be obtained the corresponding ethyl 2,3-dihydro-2-R-3-oxo-6-(4-pyridinyl)-4-pyridazinecarboxylates of Examples C-9 thru C-17.

C-9. Ethyl 2-ethyl-2,3-dihydro-3-oxo-6-(4-pyridinyl)-4-pyridazinecarboxylate.

C-10. Ethyl 2-isopropyl-2,3-dihydro-3-oxo-6-(4-pyridinyl)-4-pyridazinecarboxylate.

C-11. Ethyl 2,3-dihydro-3-oxo-2-n-propyl-6-(4-pyridinyl)-4-pyridazinecarboxylate.

C-12. Ethyl 2,3-dihydro-2-isobutyl-3-oxo-6-(4-pyridinyl)-4-pyridazinecarboxylate.

C-13. Ethyl 2-n-hexyl-2,3-dihydro-3-oxo-6-(4-pyridinyl)-4-pyridazinecarboxylate.

C-14. Ethyl 2,3-dihydro-2-(2-hydroxyethyl)-3-oxo-6-(4-pyridinyl)-4-pyridazinecarboxylate.

C-15. Ethyl 2,3-dihydro-2-(2-hydroxypropyl)-3-oxo-6-(4-pyridinyl)-4-pyridazinecarboxylate.

C-16. Ethyl 2,3-dihydro-2-(3-hydroxypropyl)-3-oxo-6-(4-pyridinyl)-4-pyridazinecarboxylate.

C-17. Ethyl 2,3-dihydro-2-(4-hydroxybutyl)-3-oxo-6-(4-pyridinyl)-4-pyridazinecarboxylate.

D. Lower-alkyl 2,3-Dihydro-2-R-3-oxo-6-PY-4-pyridazine-carboxamides

D-1. 2,3-Dihydro-2-methyl-3-oxo-6-(4-pyridinyl)-4-pyridazinecarboxamide—Ammonia was bubbled into 800 ml. of absolute ethanol with stirring over a period of 20 minutes. To the mixture was then added 50 g. of ethyl 2,3-dihydro-2-methyl-3-oxo-6-(4-pyridinyl)-4-pyridazinecarboxylate; the reaction mixture was stirred for 40 minutes and then allowed to stand at room temperature overnight. The precipitate was collected, washed with absolute ethanol, recrystallized from absolute ethanol and dried in a vacuum oven overnight to yield 15 g. of 2,3-dihydro-2-methyl-3-oxo-6-(4-pyridinyl)-4-pyridazinecarboxamide, m.p. 234°–235° C. Another 17.5 g. of product was obtained by distilling off the solvent from the mother liquor.

Acid-addition salts of 2,3-dihydro-2-methyl-3-oxo-6-(4-pyridinyl)-4-pyridazinecarboxamide are conveniently prepared by adding to a mixture of 1 g. of 2,3-dihydro-2-methyl-3-oxo-6-(4-pyridinyl)-4-pyridazinecarboxamide in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Alternatively, the lactate or hydrochloride acid-addition salt of 2,3-dihydro-2-methyl-3-oxo-6-(4-pyridinyl)-4-pyridazinecarboxamide is conveniently prepared in aqueous solution by adding to water with stirring molar equivalent quantities each of 2,3-dihydro-2-methyl-3-oxo-6-(4-pyridinyl)-4-pyridazinecarboxamide and lactic acid or hydrochloric acid, respectively.

Following the procedure described in Example D-1 but using in place of ethyl 2,3-dihydro-2-methyl-3-oxo-6-(4-pyridinyl)4-pyridazinecarboxylate a molar equivalent quantity of the appropriate ethyl 2,3-dihydro-2-R-3-oxo-6-PY-4-pyridazinecarboxylate, it is contemplated that there can be obtained the corresponding 2,3-dihydro-2-R-3-oxo-6-PY-4-pyridazinecarboxamides of Examples D-2 thru D-16.

D-2. 2,3-Dihydro-3-oxo-6-(4-pyridinyl)-4-pyridazinecarboxamide.

D-3. 2,3-Dihydro-3-oxo-6-(3-pyridinyl)-4-pyridazinecarboxamide.

D-4. 2,3-Dihydro-6-(2-methyl-3-pyridinyl)-3-oxo-4-pyridazinecarboxamide.

D-5. 2,3-Dihydro-6-(5-methyl-3-pyridinyl)-3-oxo-4-pyridazinecarboxamide.

D-6. 6-(3-Ethyl-4-pyridinyl)-2,3-dihydro-3-oxo-4-pyridazinecarboxamide.

D-7. 2,3-Dihydro-6-(2,6-dimethyl-4-pyridinyl)-3-oxo-4-pyridazinecarboxamide.

D-8. 2-Ethyl-2,3-dihydro-3-oxo-6-(4-pyridinyl)-4-pyridazinecarboxamide.

D-9. 2-Isopropyl-2,3-dihydro-3-oxo-6-(4-pyridinyl)-4-pyridazinecarboxamide.

D-10. 2,3-Dihydro-3-oxo-2-n-propyl-6-(4-pyridinyl)-4-pyridazinecarboxamide.

D-11. 2,3-Dihydro-2-isobutyl-3-oxo-6-(4-pyridinyl)-4-pyridazinecarboxamide.

D-12. 2-n-Hexyl-2,3-dihydro-3-oxo-6-(4-pyridinyl)-4-pyridazinecarboxamide.

D-13. 2,3-Dihydro-2-(2-hydroxyethyl)-3-oxo-6-(4-pyridinyl)-4-pyridazinecarboxamide.

D-14. 2,3-Dihydro-2-(2-hydroxypropyl)-3-oxo-6-(4-pyridinyl)-4-pyridazinecarboxamide.

D-15. 2,3-Dihydro-2-(3-hydroxypropyl)-3-oxo-6-(4-pyridinyl)-4-pyridazinecarboxamide.

D-16. 2,3-Dihydro-2-(4-hydroxybutyl)-3-oxo-6-(4-pyridinyl)-4-pyridazinecarboxamide.

E. 2,3-Dihydro-2-R-3-oxo-6-PY-4-pyridazinecarboxylic Acid Hydrazides

E-1. 2,3-Dihydro-3-oxo-6-(4-pyridinyl)-4-pyridazinecarboxylic Acid Hydrazide—A mixture containing 10 g. of ethyl 2,3-dihydro-3-oxo-6-(4-pyridinyl)-4-pyridazinecarboxylate and 300 ml. of absolute ethanol was heated on a steam bath with stirring for about 10 minutes. To the resulting stirred solution was added 4 g. of anhydrous hydrazine whereupon a solid began precipitating out within 5 minutes. The reaction mixture was heated for about 1 hour with stirring. The separated solid was collected, dried in a vacuum oven at 65° C. over $P_2O_5$ overnight to yield 9.4 g. of 2,3-dihydro-3-oxo-6-(4-pyridinyl)-4-pyridazinecarboxylic acid hydrazide, m.p. >300° C.

E-2. 2,3-Dihydro-2-methyl-3-oxo-6-(4-pyridinyl)-4-pyridazinecarboxylic Acid Hydrazide—This preparation was carried out following the procedure described in Example E-1 using 8.5 g. of ethyl 2,3-dihydro-2-methyl-3-oxo-6(4-pyridinyl)-4-pyridazinecarboxylate, 10.8 g. of anhydrous hydrazine and 150 ml. of ethanol. The reaction was run a second time using the same quantities of reactants. The products were combined and recrystallized from absolute ethanol to produce 10 g. of 2,3-dihydro-2-methyl-3-oxo-6-(4-pyridinyl)-4-pyridazinecarboxylic acid hydrazide, m.p. 209°–210° C. A second crop of 3 g., m.p. 212°–213° C. was obtained from the mother liquor.

Acid-addition salts of 2,3-dihydro-2-methyl-3-oxo-6-(4-pyridinyl)-4-pyridazinecarboxylic acid hydrazide are conveniently prepared by adding to a mixture of 1 g. of 2,3-dihydro-2-methyl-3-oxo-6-(4-pyridinyl)-4-pyridazinecarboxylic acid hydrazide in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Alternatively, the lactate or hydrochloride acid-addition salt of 2,3-dihydro-2-methyl-3-oxo-6-(4-pyridinyl)-4-pyridazinecarboxylic acid hydrazide is conveniently prepared in aqueous solution by adding to water with stirring molar equivalent quantities each of 2,3-dihydro-2-methyl-3-oxo-6-(4-pyridinyl)-4-pyridazinecarboxylic acid hydrazide and lactic acid or hydrochloric acid, respectively.

Following the procedure described in Example E-1 but using in place of ethyl 2,3-dihydro-3-oxo-6-(4-pyridinyl)-4-pyridazinecarboxylate a molar equivalent quantity of the appropriate ethyl 2,3-dihydro-2-R-3-oxo-6-PY-4-pyridazinecarboxylate, it is contemplated that there can be obtained the corresponding 2,3-dihydro-2-R-3-oxo-6-PY-4-pyridazinecarboxylic acid hydrazides of Examples E-3 thru E-16.

E-3. 2,3-Dihydro-3-oxo-6-(3-pyridinyl)-4-pyridazinecarboxylic acid hydrazide.

E-4. 2,3-Dihydro-6-(2-methyl-3-pyridinyl)-3-oxo-4-pyridazinecarboxylic acid hydrazide.

E-5. 2,3-Dihydro-6-(5-methyl-3-pyridinyl)-3-oxo-4-pyridazinecarboxylic acid hydrazide.

E-6. 6-(3-Ethyl-4-pyridinyl)-2,3-dihydro-3-oxo-4-pyridazinecarboxylic acid hydrazide.

E-7. 2,3-Dihydro-6-(2,6-dimethyl-4-pyridinyl)-3-oxo-4-pyridazinecaboxylic acid hydrazide.

E-8. 2-Ethyl-2,3-dihydro-3-oxo-6-(4-pyridinyl)-4-pyridazinecarboxylic acid hydrazide.

E-9. 2-Isopropyl-2,3-dihydro-3-oxo-6-(4-pyridinyl)-4-pyridazinecarboxylic acid hydrazide.

E-10. 2,3-Dihydro-3-oxo-2-n-propyl-6-(4-pyridinyl)-4-pyridazinecarboxylic acid hydrazide.

E-11. 2,3-Dihydro-2-isobutyl-3-oxo-6-(4-pyridinyl)-4-pyridazinecarboxylic acid hydrazide.

E-12. 2-n-Hexyl-2,3-dihydro-3-oxo-6-(4-pyridinyl)-4-pyridazinecarboxylic acid hydrazide.

E-13. 2,3-Dihydro-2-(2-hydroxyethyl)-3-oxo-6-(4-pyridinyl)-4-pyridazinecarboxylic acid hydrazide.

E-14. 2,3-Dihydro-2-(2-hydroxypropyl)-3-oxo-6-(4-pyridinyl)-4-pyridazinecarboxylic acid hydrazide.

E-15. 2,3-Dihydro-2-(3-hydroxypropyl)-3-oxo-6-(4-pyridinyl)-4-pyridazinecarboxylic acid hydrazide.

E-16. 2,3-Dihydro-2-(4-hydroxybutyl)-3-oxo-6-(4-pyridinyl)-4-pyridazinecarboxylic acid hydrazide.

F. 2,3-Dihydro-2-R-3-oxo-6-PY-4-pyridazinecarboxylic Acids

F-1. 2,3-Dihydro-3-oxo-6-(4-pyridinyl)-4-pyridazinecarboxylic Acid—a mixture containing 10 g. of ethyl 2,3-dihydro-3-oxo-6-(4-pyridinyl)-4-pyridazinecarboxylate and 100 ml. of 5% aqueous sodium hydroxide solution was heated on a steam bath for 6 hours, allowed to cool to room temperature and then treated slowly with acetic acid until solid began to separate. The mixture was allowed to stand until no more solid separated and the solid was then collected, dried in a vacuum oven over $P_2O_5$ at 45° C. to yield 7.7 g. of 2,3-dihydro-3-oxo-6-(4-pyridinyl)-4-pyridazinecarboxylic acid, m.p. >310° C.

F-2. 2,3-Dihydro-2-methyl-3-oxo-6-(4-pyridinyl)-4-pyridazinecarboxylic Acid—To a mixture containing diethyl hydroxy [2-oxo-2-(4-pyridinyl)ethyl]propanedioate and 40 ml. of absolute ethanol was added 4.6 g. of 1-methylhydrazine which had previously been treated with 6 ml. of 6 N hydrochloric acid. The reaction mixture was refluxed overnight and then the solvent distilled off in vacuo. The remaining yellow residue was treated with 300 ml. of 20% aqueous sodium hydroxide solution and the mixture heated on a steam bath overnight. The reaction mixture was allowed to cool to room temperature and the separated solid was collected. The solid was recrystallized from 120 ml. of acetic acid using decolorizing charcoal and the hot filtrate after removal of the decolorizing charcoal was treated with 120 ml. of hot water. The resulting solution was allowed to cool and the resulting mixture containing crystalline product was allowed to stand over the weekend. The solid was collected and dried in a vacuum oven at 80° C. over $P_2O_5$ overnight to yield 9.4 g. of 2,3-dihydro-2-methyl-3-oxo-6-(4-pyridinyl)-4-pyridazinecarboxylic acid, m.p. 267°–268° C.

Following the procedure described in Example F-1 but using in place of ethyl 2,3-dihydro-3-oxo-6-(4-pyridinyl)-4-pyridazinecarboxylate a molar equivalent quantity of the appropriate ethyl 2,3-dihydro-2-R-3-oxo-6-PY-4-pyridazine carboxylate, it is contemplated that there can be obtained the corresponding 2,3-dihydro-2-R-2,3-dihydro-3-oxo-6-PY-4-pyridazinecarboxylic acids of Example F-3 thru F-16.

F-3. 2,3-Dihydro-3-oxo-6-(3-pyridinyl)-4-pyridazinecarboxylic acid.

F-4. 2,3-Dihydro-6-(2-methyl-3-pyridinyl)-3-oxo-4-pyridazinecarboxylic acid.

F-5. 2,3-Dihydro-6-(5-methyl-3-pyridinyl)-3-oxo-4-pyridazinecarboxylic acid.

F-6. 6-(3-Ethyl-4-pyridinyl)-2,3-dihydro-3-oxo-4-pyridazinecarboxylic acid.

F-7. 2,3-Dihydro-6-(2,6-dimethyl-4-pyridinyl)-3-oxo-4-pyridazinecarboxylic acid.

F-8. 2-Ethyl-2,3-dihydro-3-oxo-6-(4-pyridinyl)-4-pyridazinecarboxylic acid.

F-9. 2-Isopropyl-2,3-dihydro-3-oxo-6-(4-pyridinyl)-4-pyridazinecarboxylic acid.

F-10. 2,3-Dihydro-3-oxo-2-n-propyl-6-(4-pyridinyl)-4-pyridazinecarboxylic acid.

F-11. 2,3-Dihydro-2-isobutyl-3-oxo-6-(4-pyridinyl)-4-pyridazinecarboxylic acid.

F-12. 2-n-Hexyl-2,3-dihydro-3-oxo-6-(4-pyridinyl)-4-pyridazinecarboxylic acid.

F-13. 2,3-Dihydro-2-(2-hydroxyethyl)-3-oxo-6-(4-pyridinyl)-4-pyridazinecarboxylic acid.

F-14. 2,3-Dihydro-2-(2-hydroxypropyl)-3-oxo-6-(4-pyridinyl)-4-pyridazinecarboxylic acid.

F-15. 2,3-Dihydro-2-(3-hydroxypropyl)-3-oxo-6-(4-pyridinyl)-4-pyridazinecarboxylic acid.

F-16. 2,3-Dihydro-2-(4-hydroxybutyl)-3-oxo-6-(4-pyridinyl)-4-pyridazinecarboxylic acid.

G. 4-Amino-6-PY-2-R-3(2H)-pyridazinones [These compounds and their preparation are disclosed and claimed in copending application Ser. No. 144,563, filed Apr. 28, 1980.]

G-1. 4-Amino-6-(4-pyridinyl-3-(2H)-pyridazinone—The following procedure described the preparation of the entitled compound from the corresponding 2,3-dihydro-3-oxo-6-(4-pyridinyl)-4-pyridazinecarboxylic acid hydrazide (Example E-1). To a mixture containing 28 g. of 2,3-dihydro-3-oxo-6-(4- pyridinyl)-4-pyridazinecarboxylic acid hydrazide and 700 ml. of concentrated hydrochloric acid and 400 ml. of water, said mixture cooled in an ice-sodium chloride bath was added a solution containing 20 g. of sodium nitrite in 75 ml. of water with vigorous stirring over a 30 minute period keeping the internal temperature below 5° C. The cold reaction mixture was stirred in the ice-salt bath for an additional 45 minutes and then at room temperature for 30 minutes and then heated gently on a steam bath. When the internal temperature reached 55°–60° C. evolution of nitrogen became rapid. The source of steam was removed until the reaction moderated. The reaction mixture was then heated on a steam bath for 2 hours and chilled in an ice bath. The separated solid was filtered off and washed with water. (See below for identification of this solid.) The combined aqueous acidic filtrate and washings were concentrated to dryness in vacuo and to the residue was added aqueous ammonium hydroxide solution until the mixture was slightly basic. The mixture was reacidified with acetic acid and cooled in an ice bath. The resulting yellow solid was collected, washed with water and dried. This solid (14.2 g.) was suspended in 50 ml. of 10% potassium bicarbonate solution, treated with 100 ml. of water and the resulting mixture stirred for 1 hour at room temperature. The yellow solid was collected, washed with water and dried in an oven at 90° C. The solid was dissolved in 300 ml. of 6 N hydrochloric acid by heating on a steam bath. The hot solution was filtered and the filtrate was allowed to stand at room temperature overnight. The bright yellow crystalline product was collected, washed with a small amount of distilled water and dried in an oven at 85° C. to yield 6.8 g. of 4-amino-6-(4-pyridinyl)-3-(2H)-pyridazinone monohydrochloride monohydrate, m.p. >340° C. The above tan solid, which had been filtered off from the acetic reaction mixture and washed with water, was dissolved in aqueous ammonium hydroxide solution and the solution filtered. The filtrate was acidified with acetic acid whereupon solid crystallized. The mixture was cooled in an ice bath. The crystalline material was collected, washed with water and dried in an oven at 80° C. to yield 13.5 g. of material, m.p. >320° C., which was identified by its NMR spectrum to be the same as Example F-1, that is, 2,3-dihydro-3-oxo-6-(4-pyridinyl)-4-pyridazinecarboxylic acid.

The above procedure of Example G-1 first procedes through the acid azide as seen by the following isolation of the acid azide as its monohydrochloride: To a solution chilled in an ice bath and containing 3.0 g. of B 2,3-dihydro-3-oxo-6-(4-pyridinyl)-4-pyridazinecarboxylic acid hydrazide and 60 ml. of 6 N hydrochloric acid was added dropwise with stirring a solution containing 3.0 g. of sodium nitrite in 10 ml. of water over a 30 minute period. The reaction mixture was then stirred for an additional 1 hour, allowing the reaction mixture to warm up to room temperature. The separated solid was collected, washed with water and dried in a vacuum oven over $P_2O_5$ at 25° C. for 48 hours to yield 3.0 g. of 2,3-dihydro-3-oxo-6-(4-pyridinyl)-4-pyridazinecarboxylic acid azide monohydrochloride, m.p. >300° C.

G-2. 4-Amino-6-(4-pyridinyl-3(2H)-pyridazinone—The following procedure describes the preparation of the entitled compound by reacting hydrazine with 6-(4-pyridinyl)-3(2H)-puridazinone, the tautomeric form of 6-(4-pyridinyl)-3-pyridazinol. A mixture containing 10 g. of 6-(4-pyridinyl)-3(2H)-pyridazinone and 70 ml. of hydrazine hydrate was heated on a steam bath for 3 days and the excess hydrazine distilled off in vacuo. The remaining residue was heated with about 300 ml. of methanol and the solid was collected by filtration. The solid was combined with the corresponding solid obtained from another run starting with 15.7 g. of 6-(4-pyridinyl)-3(2H)-pyridazinone and 21 ml. of hydrazine hydrate and the combined solids were dissolved in aqueous potassium carbonate solution and reprecipitated by addition of acetic acid. The precipitate was dried for 9 hours at 40° C. over $P_2O_5$ and then overnight at 80° C. After its NMR spectrum had shown the solid still to contain acetic acid, it was next dried in a vacuum oven at 80° C. for 2 days to yield 18.2 g. (69% yield) of 4-amino-6-(4-pyridinyl)-3(2H)-pyridazinone, m.p. >300° C.

Acid-addition salts of 4-amino-6-(4-pyridinyl)-3(2H)-pyridazinone are conveniently prepared by adding to a mixture of 1 g. of 4-amino-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochlorid, methanesulfonate, sulfate, respectively. Also, the lactate or hydrochlorid acid-addition salt of 4-amino-6-(4-pyridinyl)-3(2H)-pyridazinone is conveniently prepared in aqueous solution by adding to water with stirring molar equivalent quantities each of 4-amino-6-(4-pyridinyl)-3(2H)-pyridazinone and lactic acid or hydrochloric acid, respectively.

G-3. 4-Amino-2-methyl-6-(4-pyridinyl)-3(2H)-pyridazinone, m.p. 229°–235° C., 6.4 g., was prepared following the procedure described in Example G-2 using 12 g. of 2-methyl-6-(4-pyridinyl)-3(2H)-pyridazinone and 100 ml. of hydrazine hydrate, followed by recrystallization from acetonitrile using decolorizing charcoal.

Acid-addition salts of 4-amino-2-methyl-6-(4-pyridinyl)-3-(2H)-pyridazinone are conveniently prepared by adding to a mixture of 1 g. of 4-amino-2-methyl-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 4-amino-2-methyl-6-(4-pyridinyl)-3(2H)-pyridazinone is conveniently prepared in aqueous solution by adding to water with stirring molar equivalent quantities each of 4-amino-2-methyl-6-(4-pyridinyl)-3(2H)-pyridazinone and lactic acid or hydrochloric acid, respectively.

Following the procedure described in Example G-2 but using in place of 6-(4-pyridinyl)-3(2H)-pyridazinone a molar equivalent quantity of the appropriate 2-R-6-PY-3(2H)-pyridazinone, it is contemplated that there can be obtained the 4-amino-2-R-6-PY-3(2H)-pyridazinones of Examples G-4 thru G-22.

G-4. 4-Amino-6-(3-pyridinyl)-3(2H)-pyridazinone.

G-5. 4-Amino-6-(2-methyl-3-pyridinyl)-3(2H)-pyridazinone.

G-6. 4-Amino-6-(5-methyl-3-pyridinyl)-3(2H)-pyridazinone.

G-7. 4-Amino-6-(3-ethyl-4-pyridinyl)-3(2H)-pyridazinone.

G-8. 4-Amino-6-(2,6-dimethyl-4-pyridinyl)-3(2H)-pyridazinone.

G-9. 4-Amino-2-ethyl-6-(4-pyridinyl)-3(2H)-pyridazinone.

G-10. 4-Amino-2-isopropyl-6-(4-pyridinyl)-3(2H)-pyridazinone.

G-11. 4-Amino-2-n-propyl-6-(4-pyridinyl)-3(2H)-pyridazinone.

G-12. 4-Amino-2-isobutyl-6-(4-pyridinyl)-3(2H)-pyridazinone.

G-13. 4-Amino-2-n-hexyl-6-(4-pyridinyl)-3(2H)-pyridazinone.

G-14. 4-Amino-2-(2-hydroxyethyl)-6-(4-pyridinyl)-3(2H)-pyridazinone.

G-15. 4-Amino-2-(2-hydroxypropyl)-6-(4-pyridinyl)-3(2H)-pyridazinone.

G-16. 4-Amino-2-(3-hydroxypropyl)-6-(4-pyridinyl)-3(2H)-pyridazinone.

G-17. 4-Amino-2-(4-hydroxybutyl)-6-(4-pyridinyl)-3(2H)-pyridazinone.

G-18. 4-Amino-2-methyl-6-(3-pyridinyl)-3(2H)-pyridazinone.

G-19. 4-Amino-2-methyl-6-(2-methyl-3-pyridinyl)-3(2H)-pyridazinone.

G-20. 4-Amino-2-methyl-6-(5-methyl-3-pyridinyl)-3(2H)-pyridazinone.

G-21. 4-Amino-6-(3-ethyl-4-pyridinyl)-2-methyl-3(2H)-pyridazinone.

G-22. 4-Amino-2-methyl-6-(2,6-dimethyl-4-pyridinyl)-3(2H)-pyridazinone.

Following the procedure described in Example G-1 but using in place of 2,3-dihydro-3-oxo-6-(4-pyridinyl)-4-pyridazinecarboxylic acid hydrazide a corresponding molar equivalent quantity of the appropriate 2,3-dihydro-2-R-3-oxo-6-PY-4-pyridazinecarboxylic acid hydrazide, it is contemplated that there can be obtained as Examples G-23 thru G-41 the corresponding 4-amino-6-PY-2-R-3(2H)-pyridazinones obtained in Examples G-4 thru G-22, respectively.

G-42. 4-Amino-2-methyl-6(4-pyridinyl)-3(2H)-pyridazinone—To a solution containing 9.0 g. of sodium hydroxide in 130 ml. of water kept at 0° C. is added dropwise with stirring 2.3 ml. of bromine. To the aqueous mixture is added with stirring 8.0 g. of 2,3-dihydro-2-methyl-3-oxo-6-(4-pyridinyl)-4-pyridazincarboxamide and the resulting reaction mixture is heated on a steam bath for four hours. The reaction mixture is cooled to room temperature, acidified slowly with 6 N hydrochloric acid and the resulting acidic mixture is stirred for an additional twenty-five minutes. The acidic mixture is neutralized with 10% aqueous potassium bicarbonate solution and the mixture cooled. The precipitate is collected, washed, dried, recrystallized from acetonitrile, collected, washed with water and dried about 15 hours in a vacuum oven at 65° C. over P$_2$O$_5$ to yield 4-amino-2-methyl-6-(4-pyridinyl)-3(2H)-pyridazinone.

Following the procedure described in Example G-42 but using in place of 2,3-dihydro-2-methyl-3-oxo-6-(4-pyridinyl)-4-pyridazinecarboxamide a molar equivalent quantity of the appropriate 2,3-dihydro-3-oxo-6-PY-2-R-4-pyridazinecarboxamide, it is contemplated that there can be obtained as Examples G-43 thru G-61 the corresponding 4-amino-6-PY-2-R-3(2H)-pyridazinones obtained in Examples G-4 thru G-22, respectively.

H. 4,5-Dihydro-2-R-6-PY-3(2H)-pyridazinones [The compounds of Examples H-1 thru H-10 and H-17 thru H-21 and their preparation are disclosed and claimed in copending application Ser. No. 144,564, filed Apr. 28, 1980 and now abandoned in favor of copending application Ser. No. 243,472, filed Mar. 2, 1981.]

H-1. 4,5-Dihydro-2-methyl-6-(4-pyridinyl)-3(2H)-pyridazinone—To a stirred hot solution containing 25.6 g. of N-methylhydrazine dihydrochloride, 400 ml. of absolute ethanol and 70 ml. of water was added 32 g. of 4-oxo-4-(4-pyridinyl)butanenitrile and the resulting reaction mixture was refluxed overnight (about 15 hours). The solvent was distilled off in vacuo and the resulting solid was recrystallized from ethanol and dried in a vacuum oven at 65° C. overnight to yield 10.5 g. of 4,5-dihydro-2-methyl-6-(4-pyridinyl)-3(2H)pyridazinone as its monohydrochloride, m.p. 219°–225° C. with decomposition.

Following the procedure described in Example H-1 but using in place of N-methylhydrazine dihydrochloride a molar equivalent quantity of the appropriate N-R-hydrazine dihydrochloride or other salt of a strong inorganic acid or organic sulphonic acid, it is contemplated that there can be obtained the corresponding 4,5-dihydro-2-R-6-(4-pyridinyl)-3(2H)-pyridazinones (or salts thereof) of Examples H-2 thru H-10.

H-2. 2-Ethyl-4,5-dihydro-6-(4-pyridinyl)-3(2H)-pyridazinone.

H-3. 4,5-Dihydro-2-isopropyl-6-(4-pyridinyl)-3(2H)-pyridazinone.

H-4. 4,5-Dihydro-2-n-propyl-6-(4-pyridinyl)-3(2H)-pyridazinone.

H-5. 4,5-Dihydro-2-isobutyl-6-(4-pyridinyl)-3(2H)-pyridazinone.

H-6. 2-n-Hexyl-4,5-dihydro-6-(4-pyridinyl)-3(2H)-pyridazinone.

H-7. 2-(2-Hydroxyethyl)-4,5-dihydro-6-(4-pyridinyl)-3(2H)-pyridazinone.

H-8. 2-(2-Hydroxypropyl)-4,5-dihydro-6-(4-pyridinyl)-3(2H)-pyridazinone.

H-9. 2-(3-Hydroxypropyl)-4,5-dihydro-6-(4-pyridinyl-3(2H)-pyridazinone.

H-10. 2-(4-Hydroxybutyl)-4,5-dihydro-6-(4-pyridinyl)-3(2H)-pyridazinone. H.11. 4,5-Dihydro-6-(4-pyridinyl)-3(2H)-pyridazinone—A mixture containing 2.4 g. of 4-oxo-4-(4-pyridinyl)butanenitrile (same as γ-oxo-γ-(4-pyridinyl)butyronitrile), 1.96 g. of hydrazine sulfate, 100 ml. of absolute ethanol and 100 ml. of water was refluxed with stirring overnight (about 15 hours). The reaction mixture was heated in vacuo to remove the solvent mixture. The remaining residue was taken up in water and filtered. The filtrate was neutralized with 10% aqueous sodium bicarbonate solution and a yellow solid separated. The solid was collected, washed with water, dried in vacuo over P$_2$O$_5$ for four hours. Its nuclear magnetic resonance (nmr) and mass spectra were found to be consistent with that of the desired product but showed traces of impurities. The solid was then recrystallized from absolute ethanol, dried in vacuo over P$_2$O$_5$ overnight to yield, as golden crystals, 0.9 g. of 4,5-dihydro-6-(4-pyridinyl)-3(2H)-pyridazinone, m.p. 185°–187° C. which is tautomeric with 4,5-dihydro-6-(4-pyridinyl)-3-pyridazinol.

The above reaction also can be run by using a molar equivalent quantity of hydrazine dihydrochoride or hydrazine di(methanesulfonate) in place of hydrazine sulfate.

Acid-addition salts of 4,5-dihydro-6-(4-pyridinyl)-(2H)-pyridazinone are conveniently prepared by adding to a mixture of 1 g. of 4,5-dihydro-6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salts, e.g., hydrochloride, methanesulfonate, sulfate, respectively. Also, the lactate or hydrochloride acid-addition salt is conveniently prepared in aqueous solution by adding to water with stirring molar equivalent quantities each of 4,5-dihydro-6-(4-pyridinyl)-3(2H)-pyridazinone and lactic acid or hydrochloric acid, respectively.

Example H-11 is disclosed as its tautomeric 4,5-dihydro-6-(4-pyridinyl)-3-pyridazinol in Example 1 in each of copending applications Ser. Nos. 71,064 and 71,065, each filed Aug. 30, 1979; and, the tautomer and salts of Example H-11 are claimed in application Ser. No. 71,064.

Following the procedure described in Example H-11 but using in place of 4-oxo-4-(4-pyridinyl)butanenitrile a molar equivalent quantity of the corresponding 4-oxo-4-PY-butanenitrile, it is contemplated that there can be obtained the corresponding 4,5-dihydro-6-PY-3(2H)-pyridazinones of Examples H-12 thru H-16.

H-12. 4,5-Dihydro-6-(3-pyridinyl)-3(2H)-pyridazinone.

H-13. 4,5-Dihydro-6-(2-methyl-3-pyridinyl)-3(2H)-pyridazinone.

H-14. 4,5-Dihydro-6-(5-methyl-3-pyridinyl)-3(2H)-pyridazinone.

H-15. 6-(3-Ethyl-4-pyridinyl)-4,5-dihydro-3(2H)-pyridazinone.

H-16. 4,5-Dihydro-6-(2,6-dimethyl-4-pyridinyl)-3(1H)-pyridazinone.

Following the procedure described in Example H-1 but using in place 4-oxo-4-(4-pyridinyl)butanenitrile a molar equivalent quantity of the appropriate 4-oxo-4-PY-butanenitrile, it is contemplated that the 4,5-dihydro-6-PY-2-methyl-3-(2H)-pyridazinones of Examples H-17 through H-21 can be obtained.

H-17. 4,5-Dihydro-2-methyl-6-(3-pyridinyl)-3(2H)-pyridazinone.

H-18. 4,5-Dihydro-2-methyl-6-(2-methyl-3-pyridinyl)-3(2H)-pyridazinone.

H-19. 4,5-Dihydro-2-methyl-6-(5-methyl-3-pyridinyl)-3(2H)-pyridazinone.

H-20. 6-(3-Ethyl-4-pyridinyl)-4,5-dihydro-2-methyl-3(2H)-pyridazinone.

H-21. 4,5-Dihydro-2-methyl-6-(2,6-dimethyl-4-pyridinyl)-3(2H)-pyridazinone.

I. 2-R-6-PY-3(2H)-pyridazinones [These compounds and their preparation are disclosed and claimed in copending application Ser. No. 144,576, filed Apr. 28, 1980.]

I-1. 2-Methyl-6-(4-pyridinyl)-3(2H)-pyridazinone—To a warm solution containing 28 g. of 4,5-dihydro-2-methyl-6-(4-pyridinyl)-3(2H)-pyridazinone monohydrochloride and 140 ml. of acetic acid was added with stirring 100 ml. of bromine, and the resulting reaction mixture was refluxed overnight and then allowed to cool to room temperature. The solid that had separated was collected, stirred with 150 ml. of water and to the aqueous mixture was added sodium bisulfite until bubbling ceased. To the resulting pale yellow solution was added sufficient solid sodium bicarbonate to make it mildly basic to litmus and the resulting mixture was extracted with chloroform. The chloroform extract was heated in vacuo to remove the solvent and the resulting solid was recrystallized from methanol-ether and dried in a vacuum oven at 60° C. overnight to yield 15 g. of 2-methyl-6-(4-pyridinyl)-3(2H)-pyridazinone, m.p. 175°–185° C.

Following the procedure described in Example I-1 but using in place of 4,5-dihydro-2-methyl-6-(4-pyridinyl)-3(2H)-pyridazinone or monohydrochloride thereof a corresponding molar equivalent quantity of the appropriate 4,5-dihydro-2-R-6-(4-pyridinyl)-3(2H)-pyridazinones of Examples I-2 thru I-10 can be obtained.

I-2. 2-Ethyl-6-(4-pyridinyl)-3(2H)-pyridazinone.

I-3. 2-Isopropyl-6-(4-pyridinyl)-3(2H)-pyridazinone.

I-4. 2-n-Propyl-6-(4-pyridinyl)-3-(2H)-pyridazinone.

I-5. 2-Isobutyl-6-(4-pyridinyl)-3(2H)-pyridazinone.

I-6. 2-N-hexyl-6-(4-pyridinyl)-3-(2H)-pyridazinone.

I-7. 2-(2-Hydroxyethyl)-6-(4-pyridinyl)-3(2H)-pyridazinone.

I-8. 2-(2-Hydroxypropyl)-6-(4-pyridinyl)-3(2H)-pyridazinone.

I-9. 2-(3-Hydroxypropyl)-6-(4-pyridinyl)-3(2H)-pyridazinone.

I-10. 2-(4-Hydroxybutyl)-6-(4-pyridinyl)-3(2H)-pyridazinone.

I-11. 6-(4-Pyridinyl)-3(2H)-pyridazinone—A 2 liter 3-necked round bottom flask was equipped with a mechanical stirrer, a reflux condenser and a dropping funnel. Into the flask was placed 750 ml. of acetic acid and 16.3 g. of 4,5-dihydro-6-(4-pyridinyl)-3(2H)-pyridazinone. The mixture was heated on a steam bath for about 20 minutes and then a solution containing 50 ml. of bromine and 150 ml. of acetic acid was initially added dropwise. The first 50 ml. of solution was added over a period of about 20 minutes whereupon solid began precipitating. The rest of the bromine solution was then added all at once followed by the addition of 60 ml. more of bromine. Most of the solid redissolved and the resulting mixture was heated with stirring on a steam bath for 6 hours and then allowed to stand at room temperature over the weekend (about 65 hours). A small amount of crystalline solid was filtered off and the filtrate was heated in vacuo to remove the solvent. The remaining residue was treated with 500 ml. of boiling water whereupon most of the residue dissolved. Sodium bisulfite was added to the hot mixture until bubbling of sulphur dioxide ceased. The mixture was made weakly basic to litmus paper by adding sodium bicarbonate. The solid that separated was collected, recrystallized from isopropyl alcohol and dried in a vacuum oven over $P_2O_5$ at 45° C. for seventeen hours to produce S6.0 g. of 6-(4-pyridinyl)-3(2H)-pyridazinone hydrate (6:1), m.p. 222°–224° C.

Acid-addition salts of 6-(4-pyridinyl)-3(2H)-pyridazinone are conveniently prepared by adding to a mixture of 1 g. of 6-(4-pyridinyl)-3(2H)-pyridazinone in about 20 ml. of aqueous methanol the appropriate acid, e.g., hydrochloric acid, methanesulfonic acid, sulfuric acid, to a pH of about 2 to 3, chilling the mixture after partial evaporation and collecting the precipitated salt, e.g., hydrochloride, methanesulfonate, sulfate, respectively. Also, the lactate or hydrochloride acid-addition salt of 6-(4-pyridinyl)-3(2H)-pyridazinone is conveniently prepared in aqueous solution by adding to water with stirring molar equivalent quantities each of 6-(4-pyridinyl)-3(2H)-pyridazinone and lactic acid or hydrochloric acid, respectively.

Example I-11 is disclosed as its tuatomeric 6-(4-pyridinyl)-3-pyridazinol in Example 2 in each of copending U.S. patent applications Ser. Nos. 71,064 and 71,065, each filed Aug. 30, 1979; and, the tautomer and salts of Example I-11 are presently claimed in application Ser. No. 144,576.

Following the procedure described in Example I-11 but using in place of 4,5-dihydro-6-(4-pyridinyl)-3(2H)-pyridazinone a molar equivalent quantity of the appropriate 4,5-dihydro-6-PY-pyridazinone, it is contemplated that there can be obtained the corresponding 6-PY-3(2H)-pyridazinones of Examples I-12 thru I-16.

I-12. 4,5-Dihydro-6-(3-pyridinyl)-3(2H)-pyridazinone.

I-13. 6-(2-Methyl-3-pyridinyl)-3(2H)-pyridazinone.

I-14. 6-(5-Methyl-3-pyridinyl)-3(2H)-pyridazinone.

I-15. 6-(3-Ethyl-4-pyridinyl)-3(2H)-pyridazinone.

I-16. 6-(2,6-Dimethyl-4-pyridinyl)-3(2H)-pyridazinone.

Following the procedure described in Example I-1 but using in place of 4,5-dihydro-2-methyl-6-(4-pyridinyl)-3(2H)-pyridazinone or monohydrochloride thereof a corresponding molar equivalent quantity of the appropriate 2-methyl-6-PY-3(2H)-pyridazinone or monohydrochloride thereof, it is contemplated that the corresponding 2-methyl-6-PY-3(2H)-pyridazinones of Examples I-17 thru I-21 can be obtained.

I-17. 2-Methyl-6-(3-pyridinyl)-3(2H)-pyridazinone.

I-18. 2-Methyl-6-(2-methyl-3-pyridinyl)3(2H)-pyridazinone.

I-19. 2-Methyl-6-(5-methyl-3-pyridinyl)3(2H)-pyridazinone.

I-20. 6-(3-Ethyl-4-pyridinyl)-2-methyl-3(2H)-pyridazinone.

I-21. 2-Methyl-6-(2,6-dimethyl-4-pyridinyl)-3(2H)-pyridazinone.

J. 4-Oxo-4-PY-butanenitriles

J-1. 4-Oxo-4-(4-pyridinyl)butanenitrile—To a stirred mixture containing 29.4 g. of sodium cyanide and 500 ml. of acetonitrile, after stirring said mixture for ten minutes, was added dropwise over a period of three hours a solution containing 64.2 g. of 4-pyridinecarboxaldehyde in 500 ml. of acetonitrile and the resulting mixture was stirred at room temperature for one hour. To the stirred mixture was added slowly over a period of one hour a solution of 24.5 g. of acrylonitrile in 200 ml. of acetonitrile and the resulting reaction mixture was stirred overnight at room temperature. The reaction mixture was stripped in vacuo of solvent at a temperature not exceeding 54° C. The semi-solid residue was cooled, mixed well with 400 ml. of chloroform, and the mixture filtered. The chloroform was distilled off in vacuo at a temperature not exceeding 50° C. and the residual oily residue extracted with three 200 ml. portions of toluene. The toluene solution was filtered through diatomaceous earth and the filtrate was distilled in vacuo below 50° C. to remove the toluene. The residue on chilling crystallized. A tiny sample was saved and the remainder was dissolved in 50 ml. of warm isopropyl alcohol. The solution was cooled and then diluted slowly with 125 ml. of ether, chilled and seeded with a crystal obtained from said tiny sample. The crystalline product that separated was collected, washed with 25 ml. of 1:3 (v:v) mixture of isopropyl alcohol:ether, and air dried to yield 52.1 g. of 4-oxo-4-(4-pyridinyl)butanenitrile, m.p. 53.5°-55° C.

Following the procedure described in Example J-1 but using in place of 4-pyridinecarboxaldehyde a molar equivalent quantity of the appropriate 4- or 3-PY-carboxaldehyde, it is contemplated that there can be obtained the corresponding 4-oxo-4-PY-butanenitriles of Examples J-2 thru J-6, respectively.

J-2. 4-Oxo-4-(3-pyridinyl)butanenitrile.

J-3. 4-(2-Methyl-3-pyridinyl)-4-oxobutanenitrile.

J-4. 4-(5-Methyl-3-pyridinyl)-4-oxobutanenitrile.

J-5. 4-(3-Ethyl-4-pyridinyl)-4-oxobutanenitrile.

J-6. 4-(2,6-Dimethyl-4-pyridinyl)-4-oxobutanenitrile.

The usefulness of the compounds of formula I where R' and R" and R is lower-alkyl or lower-hydroxyalkyl, i.e., 2-R-4-R"-6-PY-3(2H)-pyridazinones, or salts thereof as cardiotonic agents is demonstrated by their effectiveness in standard pharmacological test procedures, for example, in causing a significant increase in contractile force of the isolated cat atria and papillary muscle. Detailed descriptions of these test procedures appear in U.S. Pat. No. 4,072,746, issued Feb. 7, 1980.

When tested by said isolated cat atria and papillary muscle procedure, said 2-R-4-R"-6-PY-3(2H)-pyridazinones or pharmaceutically-acceptable acid-addition salts thereof at doses of 30, 100 and/or 300 μg./ml., were found to cause significant increases, that is, greater than 25% in papillary muscle force and/or significant increases, that is, greater than 25%, in right atrial force, while causing a lower percentage increase in right atrial rate. For example, when tested at said dose levels by this procedure, the following preferred compounds were found to cause increases of 28 to 72% in papillary muscle force and/or right atrial force: the compounds of Examples C-3, D-1 and E-2.

The present invention includes within its scope a cardiotonic composition for increasing cardiac contractility, said composition comprising a pharmaceutically-acceptable carrier and, as the active component thereof, the cardiotonic compound of formula I where R' is R" and R is lower-alkyl or lower-hydroxyalkyl or pharmaceutically-acceptable acid-addition salt thereof. The invention also includes within its scope the method for increasing cardiac contractility in a patient requiring such treatment which comprises administering to such patient an effective amount of cardiotonic compound of formula I where R' is R" and R is lower-alkyl or lower-hydroxyalkyl or pharmaceutically-acceptable acid-addition salt thereof. In clinical practice said compound or salt thereof will normally be administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, e.g., lubricating agents, such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents such compositions can also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilising, preserving, wetting, emulsifying and dispersing agents.

They can be sterilized, for example, by filtration through a bacteria-retaining filter, by incorporation of sterilising agents in the composition, by irradiation or by heating. They can also be manufactured in the form of sterile solid compositions which can be dissolved in sterile water or some other sterile injectable medium immediately before use.

The percentages of active component in the said composition and method for increasing cardiac contractility can be varied so that a suitable dosage is obtained. The dosage administered to a particular patient is variable, depending upon the clinician's judgment using as the criteria: the route of administration, the duration of treatment, the size and condition of the patient, the potency of the active component and the patient's response thereto. An effective dosage amount of active component can thus only be determined by the clinician considering all criteria and utilizing the best judgement on the patient's behalf.

We claim:

1. A 2-R-4-R'-6-PY-3(2H)-pyridazinone having the formula

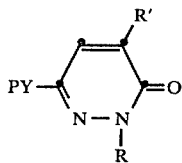

or pharmaceutically-acceptable acid-addition salt thereof, where PY is 4- or 3-pyridinyl or 4- or 3-pyridinyl having one or two lower-alkyl substituents, R is hydrogen, lower-alkyl or lower-hydroxyalkyl, and R' is carbamyl, carboxy, aminocarbamyl or lower-carbalkoxy.

2. A compound according to claim 1 where PY is 4-pyridinyl or 3-pyridinyl.

3. A compound according to claim 1 where R' is carbamyl.

4. A compound according to claim 1 where R' is aminocarbamyl.

5. A compound according to claim 1 where R' is lower-carbalkoxy.

6. A compound according to claim 1 where R is hydrogen, methyl or ethyl.

7. A cardiotonic composition for increasing cardiac contractility, said composition comprising a pharmaceutically-acceptable inert carrier and, as the active component thereof, an effective amount of a cardiotonic 2-R-4-R''-6-PY-3(2H)-pyridazinone or pharmaceutically-acceptable acid-addition salt thereof where R is lower-alkyl or lower-hydroxyalkyl, PY is 4- or 3-pyridinyl or 4- or 3-pyridinyl having one or two lower-alkyl substituents, and R'' is carbamyl, aminocarbamyl or lower-carbalkoxy.

8. The method for increasing cardiac contractility in a patient requiring such treatment which comprises administering orally or parenterally in a solid or liquid dosage form to such patient an effective amount of a cardiotonic 2-R-4-R''-6-PY-3(2H)-pyridazinone or pharmaceutically-acceptable acid-addition salt thereof, where R is lower-alkyl or lower-hydroxyalkyl, PY is 4- or 3-pyridinyl or 4- or 3-pyridinyl having one or two lower-alkyl substituents, and R'' is carbamyl, aminocarbamyl or lower-carbalkoxy.

* * * * *

UNITED STATES PATENT AND TRADEMARK OFFICE
CERTIFICATE OF CORRECTION

PATENT NO. : 4,304,776
DATED : December 8, 1981
INVENTOR(S) : George Y. Lesher and William B. Dickinson It is certified that error appears in the above-identified patent and that said Letters Patent are hereby corrected as shown below:

Column 1, line 68, "996v" should read -- 096v --.

Column 2, line 62, "-3-(2H)" should read -- -3(2H) --.

Column 6, line 67 "hydrazine" (first occurrence) should read -- hydrazide --.

Signed and Sealed this

Thirty-first Day of August 1982

[SEAL]

Attest:

Attesting Officer

GERALD J. MOSSINGHOFF
Commissioner of Patents and Trademarks